(12) United States Patent
Hiromoto

(10) Patent No.: US 7,019,036 B2
(45) Date of Patent: Mar. 28, 2006

(54) ENVIRONMENTALLY FRIENDLY PESTICIDE COMPOSITIONS

(75) Inventor: Bryan Hiromoto, Honolulu, HI (US)

(73) Assignee: ABR, LLC, Honolulu, HI (US)

( * ) Notice: Subject to any disclaimer, the term of this patent is extended or adjusted under 35 U.S.C. 154(b) by 217 days.

(21) Appl. No.: 10/602,318

(22) Filed: Jun. 23, 2003

(65) Prior Publication Data
US 2004/0127362 A1    Jul. 1, 2004

Related U.S. Application Data

(60) Provisional application No. 60/390,289, filed on Jun. 21, 2002.

(51) Int. Cl.
*A01N 25/02* (2006.01)
*A01N 63/02* (2006.01)
*A01N 65/00* (2006.01)

(52) U.S. Cl. .............. 514/775; 514/777; 514/938; 426/582; 426/585; 426/602

(58) Field of Classification Search ............... 504/313, 504/350; 514/511, 529, 775, 777, 938; 426/582, 426/585, 602
See application file for complete search history.

(56) References Cited

U.S. PATENT DOCUMENTS 5,998,484 A * 12/1999 Zobitne et al. ............. 514/711
6,548,085 B1 * 4/2003 Zobitne et al. ............. 424/725

FOREIGN PATENT DOCUMENTS

WO    WO 01/74161    4/2001

* cited by examiner

*Primary Examiner*—S. Mark Clardy
(74) *Attorney, Agent, or Firm*—Morrison & Foerster LLP

(57) ABSTRACT

Pesticidal compositions which are environmentally safe, consisting essentially of a minimum risk pesticide in combination with one or more inert ingredients are disclosed.

13 Claims, No Drawings

ENVIRONMENTALLY FRIENDLY PESTICIDE COMPOSITIONS

CROSS-REFERENCE TO RELATED APPLICATION

The present application is related to and claims priority to U.S. patent application Ser. No. 60/390,289, filed date of 21 Jun. 2002. The contents of this document is incorporated herein by reference.

TECHNICAL FIELD

The invention relates to pesticides, particularly nematocides, that employ only ingredients which are free from pesticide registration requirements. More particularly, the invention relates to compositions which can be applied agriculturally directly onto plants or their surroundings which employ only ingredients that are considered completely safe for the environment.

BACKGROUND ART

PCT application PCT/US01/10982, filed 4 Apr. 2001 and published as WO 01/74161 incorporated herein by reference describes pesticidal complexes that are particularly effective with regard to nematodes and penetrants that can be used for various purposes, including as components of the pesticidal compositions. The penetrant surfactant composition consists essentially of at least one linear alcohol of 7–12C which is polyalkoxylated, at least one microemulsion-enhancing component and at least one anionic detergent. This penetrant composition can be used in combination with the nematocidal or pesticidal components in agriculture as well as in alternative uses such as topical formulations for pharmaceutical or veterinary use. The pesticidal compositions themselves contain, in addition to the components of the penetrant either a lipase associated with at least one $C_{16}$–$C_{20}$ monounsaturated fatty acid or ester (including vegetable oils) or a saccharide esterified to at least one monounsaturated $C_{16}$–$C_{20}$ fatty acid. These compositions, because they contain penetrants which may not be recognized as as safe as they actually are, require approval from the Environmental Protection Agency in the United States in order to be sold. In addition, the above-mentioned lipase may be derived from a fungal culture, and the complexities and uncertainties of the components of such cultures prevents their being recognized as safe. It would be desirable to formulate pesticides which are composed entirely of recognized "safe" ingredients that are environmentally friendly. If desired, of course, the compositions could be mixed with penetrants such as those described in WO 01/74161 when they are applied to the soil. This publication also describes methods to use nematacides and pesticides that are applicable to the nematacides and pesticides of the present invention.

The present invention is directed to such compositions.

DISCLOSURE OF THE INVENTION

The invention is directed to pesticides, in particular nematocides, that consist only of recognized minimal risk pesticide components and recognized inert components. The pesticides of the invention are applied as diluted solutions so that their delivery is exclusively through direct physical contact with the agricultural pest, in particular, nematodes. It is important that no vapor components be present as that would defeat the purpose of constructing environmentally friendly compositions.

Thus, in one aspect, the invention is directed to a pesticidal composition consisting essentially of one or more minimal risk pesticides and optionally one or more inert substances. The invention also includes forms of this composition which have been diluted with water. In another aspect, the invention is directed to a method to control agricultural pests which method comprises applying the compositions of the invention or diluted forms thereof to an area in which such control is desired.

MODES OF CARRYING OUT THE INVENTION

The Environmental Protection Agency of the United States issues regulations set forth in 40 Code of Federal Regulations (40 C.F.R.) and those sections pertinent to pesticides are in subchapter E, sections 152–180. In order to protect the public, pesticides for application to agricultural sites must be registered, unless they contain only ingredients which are excepted from the registration procedure. These exceptions are updated from time to time and current lists may be obtained from the Environmental Protection Agency website, www.EPA.gov/pesticides.

There are two types of exemptions that are relevant to the present invention. The first is a set of "minimum risk pesticides."

The relevant information concerning the minimum risk pesticides is as follows:

The 25b List 40 C.F.R. § 152.25(g) Minimum risk pesticides—(1) Exempted products. Products containing the following active ingredients are exempt from the requirements of FIFRA, alone or in combination with other substances listed in this paragraph, provided that all of the criteria of this section are met. Castor oil (U.S.P. or equivalent) Cedar oil Cinnamon and cinnamon oil Citric acid Citronella and Citronella oil Cloves and clove oil Corn gluten meal Corn oil Cottonseed oil Dried Blood Eugenol Garlic and garlic oil Geraniol Geranium oil Lauryl sulfate Lemongrass oil Linseed oil Malic acid Mint and mint oil Peppermint and peppermint oil 2-Phenethyl propionate (2-phenylethyl propionate) Potassium sorbate Putrescent whole egg solids Rosemary and rosemary oil Sesame (includes ground sesame plant) and sesame oil Sodium chloride (common salt) Sodium lauryl sulfate Soybean oil Thyme and thyme oil White pepper Zinc metal strips (consisting solely of zinc metal and impurities) (2) Permitted inerts. A pesticide product exempt under paragraph (g)(1) of this section may only include inert ingredients listed in the most current List 4A. This list is updated periodically and is published in the Federal Register. The most current list may be obtained by writing to: Registration Support Branch (4A Inerts List) Registration Division (7505C), Office of Pesticide Programs, Environmental Protection Agency, 401 M St., SW., Washington D.C. 20460. (3) Other conditions of exemption. All of the following conditions must be met for products to be exempted under this section: (i) Each product containing the substance must bear a label identifying the name and percentage (by weight) of each active ingredient and the name of each inert ingredient. (ii) The product must not bear claims either to control or mitigate microorganisms that pose a threat to human health, including but not limited to disease transmitting bacteria or viruses, or claims to control insects or rodents carrying specific diseases, including, but not limited to ticks that carry Lyme disease. (iii)

The product must not include any false and misleading labeling statements, including those listed in 40 CFR 156.10(a)(5)(i) through (viii).

The relevant information concerning "inert ingredients" is as follows:

List 4A inert ingredients are considered to be minimal risk inert ingredients. List 4A is generally reserved for those substances that are common foods or substances that are ubiquitous in nature and are not expected to present a hazard to human health or the environment. In a final rule published in the Federal Register on Mar. 6, 1996 (61 FR 8876), certain pesticidal substances were exempted from regulation as active ingredients under section 25(b) of the Federal Insecticide, Fungicide and Rodenticide Act, and List 4A inert ingredient were designated as inert ingredients that could be formulated with exempted active ingredients without jeopardizing the exempted status of the pesticide product. List 4A inert ingredients were identified in a Federal Register notice published on Sep. 28, 1994 (59 FR 49400). A FR notice identifying substances for addition to List 4A is expected in the near future. A-B-C-D-E-F-G-H-I-J-K-L-M-N-O-P-Q-R-S-T-U-V-W-X-Y-Z-A- Acetic acid Agar Alfalfa Alfalfa meal Almond hulls Almond shells Alpha cellulose Apple pomace Attapulgite-type clay -B- Beef fat Beeswax Beet powder Bentonite Bone Meal Bran Bread crumbs -C- Calcareous shale Calcite Calcium carbonate Canary seed Cane syrup Carbon dioxide Cardboard Carrageenan Carrots Casein Cheese Chlorophyll Cinnamon Citric acid Citrus meal Citrus pectin Citrus pulp Clam shells Cloves Cocoa Cocoa shells Coco shell flour Cod liver oil Coffee grounds Cookies Cork Corn Corn cobs Corn flour Corn meal Corn oil Cornstarch Corn syrup Cotton Cottonseed meal Cottonseed oil Cracked oats Cracked wheat -D- Dextrin Dextrose Dolomite Douglas-fir bark, ground -E- Eggs Egg Shells Edible fish meal Edible fish oil -F- Flour Fuller's earth -G- Gelatin Glue, as depolyrnerized animal collagen Glycerin Granite Grape pomace Graphite Ground oats Guar gum Gum arabic Gum tragacanth Gypsum -H- Hearts of corn flour Hydrogenated vegetable oils Honey -I- Invert sugar Invert syrup -K- Kaolinite-type clay -L- Lactose Lanolin Lard Latex Lecithin Lime Limestone Linseed oil -M- Malt flavor Meat meal Meal scraps Medicated feed Mica Milk Millet seed Mineral oil, U.S.P. Molasses Montmorillonite-type clay -N- Nitrogen Nutria meat Nylon -O- Oatmeal Oats Olive oil Onions Orange pulp Oyster shells -P- Paper Paprika Paraffin wax Peanut butter Peanut oil Peanuts Peanut shells Peat moss Pecan shell flour Pectin Polyethylene film Polyethylene pellets Potatoes Pumice -R- Raisins Red cedar chips Red dog flour Rice Rice hulls Rubber Rye Flour -S- Safflower oil Sawdust Seaweed, edible Shale Soapstone Sodium bicarbonate Sodium chloride Sorbitol Soybean hulls Soybean meal Soybean oil Soy flour Soy protein Sucrose Sugarbeet meal Sunflower seeds -T- Tallow -V- Vanillin Vermiculite Vitamin C Vitamin E -W- Walnut flour Walnut shells Water Wheat Wheat germ oil Whey Wintergreen oil Wool -X- Xanthan gum -Y- Yeast.

The pesticide compositions of the invention typically contain at least one "minimum risk" pesticide; preferred among these are sodium lauryl sulfate, lauryl sulfate and various oils, including castor oil, cedar oil, cinnamon oil, cottonseed oil, sesame oil and the like. The oils may be used alone, or may be combined with "inert ingredients" such as cheese, molasses, or other ingredients on the list set forth above. It will be noted that various oils appear on both lists, and it is arbitrary whether they are to be designated in a particular composition as a pesticide having minimal risk or an inert ingredient.

In one typical composition, the active ingredient, sodium lauryl sulfate is dissolved or suspended in the inert ingredients. The inert ingredients, considered the solvent or suspending solvent, may include mixtures of oil and molasses and may further include small amounts of cheese as cheese is considered an inert ingredient.

In another approach, as oils are considered active ingredients, they can be employed as such either as single oils or as mixtures, and optionally in combination with small amounts of cheese. For use, these compositions are typically sold separately, but when used, combined with a penetrant such as that described in the above-cited WO 01/74161.

For application of the compositions, they are typically diluted in water and sprayed or poured onto the soil. Specific concentrations of active ingredient in the aqueous solution range from 0.5% to about 15%, typically 1%–10%, and more typically about 2–3%. Specific percentages and approaches to application will vary with the type of crop, and are readily optimized using the methods known to the skilled artisan.

The following example is intended to illustrate, but not limit the invention.

EXAMPLE 1

Safe Pesticide Formulation

Ingredients:

| Active ingredient | Sodium lauryl sulphate | 8% w/v |
|---|---|---|
| Inert ingredients | Molasses | 90% v/v |
| | Safflower Oil | 10% v/v |
| | Cheese | 0.001% w/v |

Usage

A 1% solution may be made by mixing one gallon of the material with 100 gallons of water. Stir until a foamy head occurs, this indicates that the surfactant has dissolved and that the solution is ready to be used. Do not store for more than 24 hours once mixed with water, use diluted mixture immediately if possible. Unopened concentrate may be stored in a cool dry place for a year.

This material may be used as a preplant or postplant nematicide. This material may also kill soil insects on contact when used as a 2% solution. Test for phytotoxicity on a small crop sample since material may also kill germinating seeds and seedlings. This material has limited preemergence herbicidal properties for monocots and dicots.

Coffee: 1% solution applied as a soil drench to 8-inch tall seedlings or older plants. 2% solution may be applied as a soil drench 3 weeks prior to planting as a preplant soil treatment.

Corn: Avoid applying to germinating seeds or to 6-inch tall seedlings. 1% solution applied as a soil drench to 12-inch tall seedlings or older plants. 2% solution may be applied as a soil drench 3 weeks prior to planting.

Papaya: 1% solution applied as a soil drench to 8-inch tall seedlings or older plants. 2% solution may be applied as a soil drench 3 weeks prior to planting. A 2% solution is phytotoxic to papaya seedlings when applied directly.

Pineapples: 1% solution applied as a postplant soil drench to crowns or slip plantings. 2% solution may be applied as a soil drench 3 weeks prior to planting as a preplant application. Pineapples can tolerate up to an 8% solution as a postplant application. Calculate quantities based on a quart to 2 quart of diluted solution per plant depending on the concentration used.

1% solution—use 2 quarts per plant

2% or higher solution—use 1 quart per plant.

Do not apply to wet soil. Soil must be dry in order for the material to penetrate the dry soil particles and kill the nematodes.

Protea: 1% solution applied as a soil drench to 8-inch tall seedlings or older plants. 2% solution may be applied as a soil drench 3 weeks prior to planting as a preplant soil treatment.

Strawberries: A 2% solution may be applied as a preplant or postplant soil drench to 5 inch diameter or larger transplants.

Turfgrass: 1% solution applied as a soil drench 30 days apart.

Some turfgrass may tolerate a 4% solution. Pretest a small area for phytotoxicity prior to a large application.

Vegetables and Ornamentals: 1% solution applied as a soil drench to 6-inch tall seedlings or older plants. 2% solution may be applied as a preplant soil drench 3 weeks prior to planting.

Quantity to apply: Amount to apply will vary with the root depth of the plant. Small vegetable plants may require only a quart of diluted material per plant. Larger plants such as full grown papaya or coffee trees may require 10 gallons of the diluted material per tree.

Application Timing: Preplant application 3 weeks prior to planting, Post plant application 6 weeks after planting or when the plants are old enough not to show phytotoxicity. Second postplant application 4 weeks later to kill any surviving eggs and larvae.

Sample Timeline:

| | |
|---|---|
| Preplant Application | 3 weeks prior to planting |
| No Application | Planting |
| First Post Plant Application | 6 weeks after planting |
| Second Application | 4 weeks after the first postplant |

WARNING: Avoid applying directly to germinating seeds or to seedling stages. Test with a few seedlings for phytotoxic effects. Certain vegetables are very sensitive to this material.

The invention claimed is:

1. A nematocide formulation consisting essentially of an aqueous medium containing 0.5%–15% v/v of a composition consisting essentially of one or more oils in combination with molasses and/or cheese, wherein said one or more oils is present in a nematocidally effective amount.

2. The formulation of claim 1, wherein the one or more oils are vegetable oils.

3. The formulation of claim 2, wherein the vegetable oil is one or more of castor oil, cedar oil, cinnamon oil, cottonseed oil, sesame oil or safflower oil.

4. The formulation of claim 3, wherein said oil is combined with cheese.

5. The formulation of claim 1, wherein said oil is combined with cheese.

6. The formulation of claim 5, wherein the oil is safflower oil.

7. The formulation of claim 1, which contains 2%–3% v/v of said composition.

8. A method to control nematode agricultural pests which method comprises applying the formulation of claim 7 to an area in which such control is desired.

9. A method to control nematode agricultural pests which method comprises applying the formulation of claim 1 to an area in which such control is desired.

10. A method to control nematode agricultural pests which method comprises applying the formulation of claim 6 to an area in which such control is desired.

11. Dry soil to which has been applied the formulation of claim 1.

12. Dry soil to which has been applied the formulation of claim 6.

13. Dry soil to which has been applied the formulation of claim 7.

* * * * *